(12) United States Patent
Dela (10) Patent No.: US 9,820,844 B2
(45) Date of Patent: Nov. 21, 2017

(54) DOUBLE CONICAL IVC FILTER

(71) Applicant: Cook Medical Technologies LLC, Bloomington, IN (US)

(72) Inventor: Christian Dela, Valby (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 209 days.

(21) Appl. No.: 14/932,357

(22) Filed: Nov. 4, 2015

(65) Prior Publication Data

US 2016/0128820 A1 May 12, 2016

Related U.S. Application Data (60) Provisional application No. 62/076,515, filed on Nov. 7, 2014.

(51) Int. Cl.
  *A61F 2/01* (2006.01)
(52) U.S. Cl.
  CPC .......... *A61F 2/01* (2013.01); *A61F 2002/016* (2013.01); *A61F 2250/001* (2013.01)
(58) Field of Classification Search
  CPC  A61F 2/01; A61F 2002/016; A61F 2002/011; A61F 2002/015; A61F 2/013; A61B 17/221
  See application file for complete search history.

(56) References Cited

U.S. PATENT DOCUMENTS

| | | | |
|---|---|---|---|
| 5,733,294 A | 3/1998 | Forber et al. | |
| 7,749,243 B2 | 7/2010 | Phung et al. | |
| 7,959,647 B2 | 6/2011 | Palmer | |
| 7,972,359 B2 | 7/2011 | Kreidler | |
| 8,535,344 B2 | 9/2013 | Linder et al. | |
| 8,734,480 B2 | 5/2014 | Snow | |
| 2002/0111648 A1* | 8/2002 | Kusleika | A61F 2/01 606/200 |

(Continued)

FOREIGN PATENT DOCUMENTS

| WO | WO 01/10342 A1 | 2/2001 |
|---|---|---|
| WO | WO 2008/127328 A1 | 10/2008 |
| WO | WO 2010/091118 A1 | 8/2010 |

OTHER PUBLICATIONS

Extended European Search Report dated Apr. 16, 2015.
Cardinal Search Report dated Jul. 11, 2014.

*Primary Examiner* — Eric Rosen
*Assistant Examiner* — Brooke Labranche
(74) *Attorney, Agent, or Firm* — Brinks Gilson & Lione (57) ABSTRACT

The disclosure provides an IVC filter device and method to filter. The device has a first bar and a first slider. The first slider has a first bore formed therethrough slidably disposed on the first bar. The device further comprises a second bar and a second slider. The second slider has a second bore formed therethrough and slidably disposed on the second bar. The device further has a first set of filter struts with a first filter strut being arcuate and attached to the first bar. The first filter strut may extend to the second slider. In addition, a second set of filter struts has a second filter strut being arcuate and attached to the second bar, extending to the first slider. When disposed in the vena cava, the device may receive a force through its filter struts and slide one of the sliders to accommodate the force.

20 Claims, 7 Drawing Sheets

(56) References Cited

U.S. PATENT DOCUMENTS

| | | |
|---|---|---|
| 2004/0127935 A1 | 7/2004 | VanTassel et al. |
| 2004/0138692 A1 | 7/2004 | Phung et al. |
| 2004/0186512 A1 | 9/2004 | Bruckheimer et al. |
| 2009/0204143 A1 | 8/2009 | Park et al. |
| 2009/0299403 A1 | 12/2009 | Chanduszko et al. |
| 2013/0184737 A1 | 7/2013 | Cully et al. |
| 2013/0345740 A1 | 12/2013 | Angel et al. |
| 2014/0180330 A1 | 6/2014 | Angel et al. |
| 2014/0200608 A1 | 7/2014 | Brady et al. |

* cited by examiner

FIG. 7

DOUBLE CONICAL IVC FILTER

CROSS-REFERENCE TO RELATED APPLICATIONS

This application is a claims benefit of U.S. Provisional Patent Application No. 62/076,515, filed Nov. 7, 2014, entitled "DOUBLE CONICAL IVC FILTER." The entire contents of which are incorporated herein by reference.

BACKGROUND

1. Technical Field

The present disclosure relates to medical devices. More particularly, the disclosure relates to a double conical vena cava filter and method of treatment with said device in the body.

2. Background Information

The vena cava is the largest vein in the body. This vein returns deoxygenated blood to the heart. Due to the vena cava's location, its structure is flexible as it moves with heartbeat and the diaphragm during breathing. Vena cava filters are common prophylactic devices to prevent pulmonary embolisms caused by deep vein thrombosis. Such filters can be placed using minimally invasive techniques either from the jugular or femoral vein. Such filters may operate to prevent pulmonary embolism.

Because the vena cava is highly flexible, current filters may not provide the desired flexibility to maintain the natural physiology of the vena cava. There is a need for a device that may respond to the vena cava's flexible environment and distribute or redistribute forces on the vena cava while still maintaining filtering capacity.

BRIEF SUMMARY

The present disclosure provides generally for a double conical IVC filter and a method of treatment in a body vessel, the body vessel having a vessel wall. The device may include a first bar with a first end having a first end cap and extending distally along a first longitudinal length $L_{B1}$ to a second end having a first center cap. The device may also include a second bar with third end having a second end cap and extending proximally along a second longitudinal length $L_{B2}$ to a fourth end having a second center cap, the first end cap being disposed proximal to the second end cap.

The device may include a first slider having a first slider body with a first bore formed therethrough defining a first opening and a second opening. The first bar may be slidably disposed through the first and second openings to allow play between the first bar and first slider. The device may also include a second slider having a second slider body with a second bore formed therethrough defining a third opening and a fourth opening, the second bar slidably disposed through the third and fourth openings to allow play between the second bar and second slider.

The device further includes a first set of filter struts and a second set of filter struts. The first set of filter struts may have a first filter strut being arcuate and having a first portion attached to the first end cap and extending distally to a second portion, the second portion being attached to the second slider. The second set of filter struts may have a second filter strut being arcuate and having a third portion attached to the second end cap and extending proximally to a fourth portion, the fourth portion being attached to the first slider. Each filter strut may have a contact portion to contact the vessel wall wherein the first and second sets of filter struts allow accommodation of body vessel movement.

The first bar may be cylindrical to complement the first bore. In addition, the second bar may be cylindrical to complement the second bore. The first slider may have a length $L_{S1}$ and a second slider may have a length $L_{S2}$, the length $L_{S1}$ may be shorter than the first longitudinal length $L_{B1}$ and the length $L_{S2}$ may be shorter than the second longitudinal length $L_{B2}$.

The first bar may include a first track formed between a proximal track end and the first center cap. In addition, the second bar may include a second track formed between the second center cap and a distal track end. The first slider may be slidably disposed in the first track and the second slider may be slidably disposed in the second track. In this embodiment, the first bore may be formed complementary to the first track to maintain the first slider in the first track. In addition, the second bore may be formed complementary to the second track to maintain the second slider in the second track.

The first portion may be disposed about 45 degrees circumferentially from the fourth portion, and the second portion may be disposed about 45 degrees circumferentially from the third portion. The first end cap may have a plurality of first portions disposed circumferentially and equally spaced around the first end cap. In addition, the second slider may have a plurality of second portions disposed circumferentially and equally spaced around the second slider. The second end cap may have a plurality of third portions disposed circumferentially and equally spaced around the second end cap. The first slider may have a plurality of forth portions disposed circumferentially and equally spaced around the first slider. The first set of filter struts may be four filter struts and the second set of filter struts may be four filter struts. Each filter strut may contain Elgiloy or Nitinol.

The device may have a first hook attached to the first end cap and a second hook attached to the second end cap. In addition, each filter strut may include a barb adjacent to the contact portion to secure the device to the vessel wall.

As one advantage of the present disclosure, the device may respond to the natural movements of the vena cava due to the slidable play between the sliders and the bars. In addition, the independent nature of the two sets of filter struts may allow the filter to respond to the forces of the vena cava, while maintaining a self-centered or self-correcting position in response to these forces. The contact portions of the device may provide stability and centering to avoid unintended tilting.

As an additional advantage, the dual conical device may provide dual or increased filtering capacity. In addition, the two sets of filter struts operate bi-directionally so that the device may be used to filter from either the proximal or distal side of the device.

The present disclosure also provides a method of treatment. The method may include: disposing the device, as described herein, within the body vessel; receiving a force on the contact portion of one filter strut of the first set and the second set of filter struts, possibly caused by body vessel movement; and sliding one of the first slider along the first bar and the second slider along the second bar to accommodate of the force. The step of sliding may include the first slider sliding along the first bar between the first end cap and the first center cap. The step of sliding may include the second slider sliding along the second bar between the second center cap and the second end cap.

The step of disposing may include disposing the device wherein the first bar has a first track formed between a proximal track end and the first center cap and the second bar has a second track formed between the second center cap and a distal track end. The first slider may be slidably disposed in the first track and the second slider is slidably disposed in the second track. The step of sliding may include the first slider sliding in the first track between the proximal track end and the first center cap. The step of sliding may further include the second slider sliding in the second track between the second center cap and the distal track end.

DETAILED DESCRIPTION

The present invention provides a double conical IVC filter for filtering in a body vessel. The disclosure provides also for methods of treatment or filtering using the device. The materials, methods, and examples disclosed herein are illustrative only and not intended to be limiting. The disclosed figures are not necessarily to scale.

All publications, patent applications, patents, and other references mentioned herein are incorporated by reference in their entirety. Unless otherwise defined, all technical and scientific terms used herein have the same meaning as commonly understood by one of ordinary skill in the art to which this disclosure pertains. In the case of conflict, the present document and definitions will control.

"Complement," "complementary," or derivatives thereof will be understood to mean corresponding, pairing, or matching, such as corresponding in shape.

The terms "proximal" and "distal" and derivatives thereof will be understood in the frame of reference of a medical physician using the device. Thus, proximal refers to locations closer to the physician and distal refers to locations farther away from the physician (e.g., deeper in the patient's vasculature).

Figures 1A, 1B, 1C:
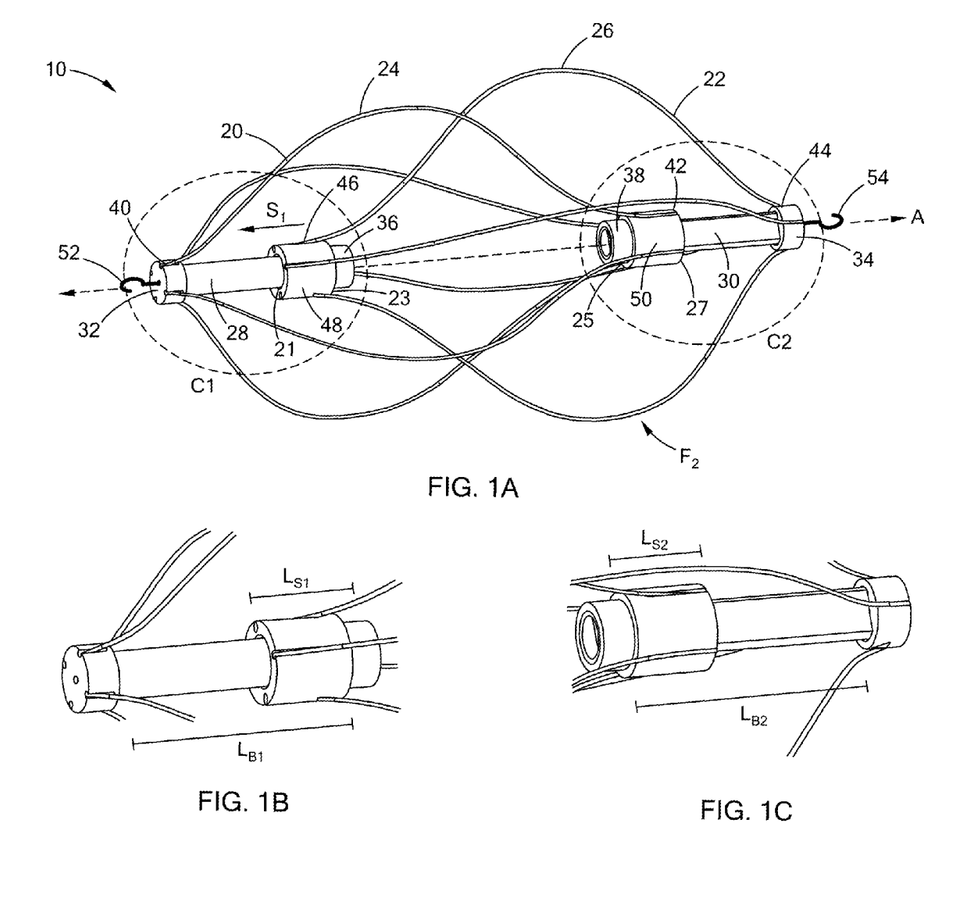
FIGS. 1A-1C are side views of a medical device for filtering in a body vessel in accordance with one embodiment of the present invention.

FIGS. 1A-1C illustrate a first embodiment of the device 10. In this embodiment, the device has a first bar 28 having a first end comprising a first end cap 32 and extending distally along a first longitudinal length to a second end comprising a first center cap 36. The device further comprises a second bar having a third end comprising a second end cap 34 and extending proximally along a second longitudinal length to a fourth end comprising a second center cap 38. The first end cap 32 may be disposed proximal to the second end cap 34.

In this embodiment, the device further comprises a first slider 48 having a first slider body with a first bore formed therethrough along the longitudinal axis A of the device. The first bore defines a first opening 21 and a second 23 opening. The first bar 28 may be slidably disposed through the first and second openings (21 and 23, respectively) to allow play between the first bar 28 and the first slider 48. The second slider 50 may have a second slider body with a second bore formed therethrough along the longitudinal axis A, defining a third opening 25 and a fourth opening 27. The second bar 30 may be slidably disposed through the third opening 25 and fourth opening 27 to allow play between the second bar 30 and the second slider 50.

The device further comprises a first set of filter struts and a second set of filter struts opposite the first set. The first set of filter struts comprises a first filter strut 20 being arcuate and having a first portion 40 attached to the first end cap 32 and extending distally to a second portion 42. The second portion 42 may be attached to the second slider 50. The second set of filter struts comprises a second filter strut 22 being arcuate and having a third portion 44 attached to the second end cap 34 and extending proximally to a forth portion 46. The forth portion 46 may be attached to the first slider 48.

The attachment of the filter struts to the sliders and end caps may be through any method known in the art including gluing, soldering, welding, or clamping. In one example, the first portion 40 may be fed through a hole or opening in the first end cap 32 and clamped inside the first end cap 32 to secure the first filter strut 20. This type of attachment may be employed for attaching any portion discussed herein.

Each filter strut may have a contact portion to contact the vessel wall wherein the first and second sets of filter struts allow accommodation of body vessel movement. On the first filter strut 20, the contact portion 24 may contact the vessel wall. On the second filter strut 22, the contact portion 26 may contact the vessel wall. A force on a filter strut may slide a slider to accommodate that force. As shown in FIG. 1A, force $F_2$ pushes on the second set of filter struts and slides or moves the first slider proximally in the direction of arrow $S_1$.

In one embodiment, the first bar 28 and the second bar 30 may be cylindrical to complement the first bore and the second bore, respectively. In addition, the device may further comprise a first hook 52 attached to the first end cap 32 and a second hook 54 attached to the second end cap 34. One skilled in the art will understand that the device may comprise no hooks, one hook of the first and second hooks, or both the first and second hooks as desired.

FIG. 1B is a blown-up view of FIG. 1A in circle $C_1$. This blown-up view depicts the proximal end of the device. Here, the first bar has a first longitudinal length $L_{B1}$ and the first slider has a length $L_{S1}$. Likewise, FIG. 1C shows a blown-up view of circle $C_2$ in FIG. 1A. In this view, the second bar has a second longitudinal length $L_{B2}$ and the second slider has a length of $L_{S2}$. The length $L_{S1}$ may be shorter than the first longitudinal length $L_{B1}$ and the length $L_{S2}$ may be shorter than the second longitudinal length $L_{B2}$. In one embodiment, the first longitudinal length and the second longitudinal length are about 10 millimeters each. In one embodiment, the total length of the device from first hook to second hook is about 50 millimeters.

Figure 2:
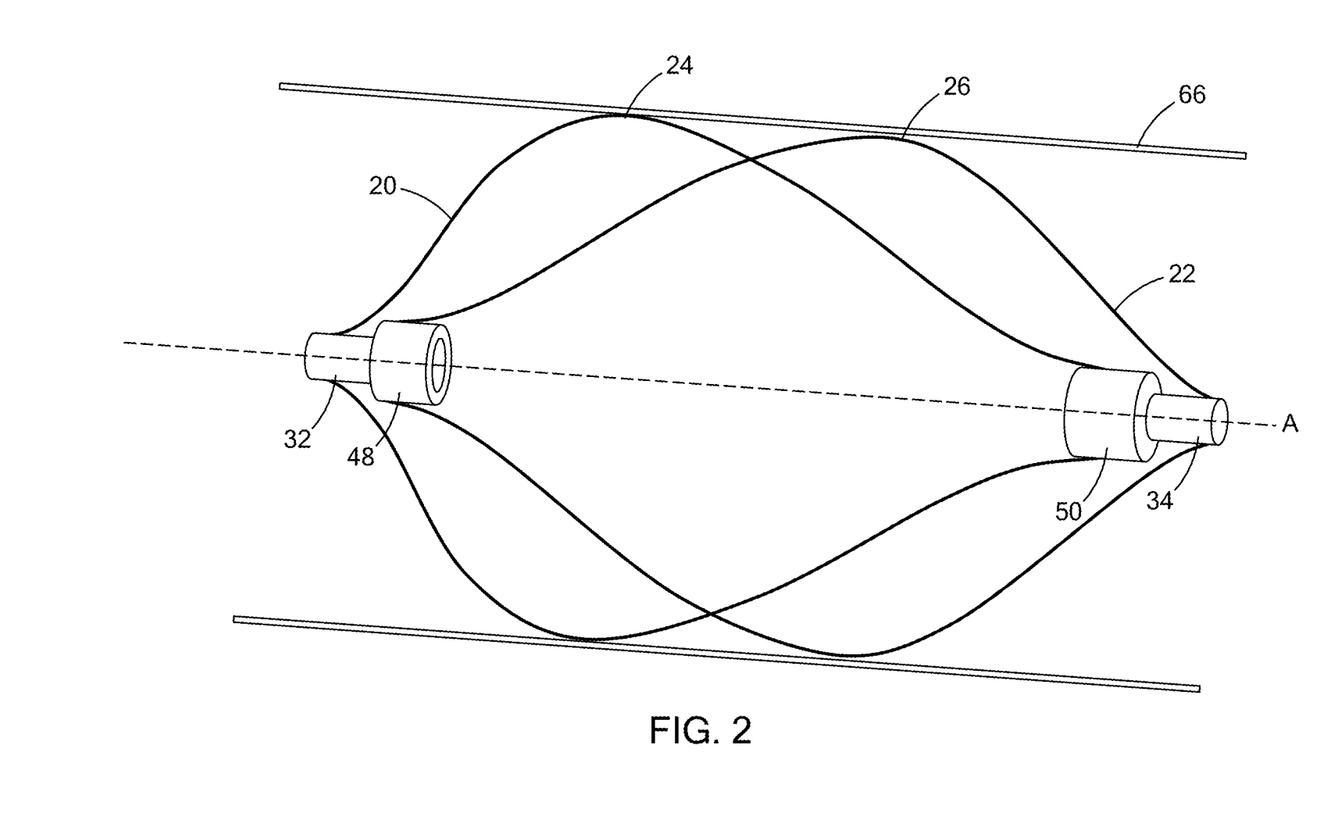
FIG. 2 is an environmental partial side view of the device of FIG. 1A.

FIG. 2 depicts an environmental view of part of the device against the vessel wall 66. Here, the contact portions 26, 24 contact the vessel wall for stability and maximum filtering. It will be understood that each filter strut in the device may have a contact portion. In one embodiment, the first set of filter struts comprises four filter struts and a second set of filter struts comprises four filter struts, totaling 8 filter struts.

The filter struts may be made of any material known in the art for this intended purpose. In one embodiment, each filter strut comprises Nitinol or Elgiloy. Nitinol is a metal alloy of nickel and titanium having unique shape memory setting properties and being biocompatible. At a transition temperature, Nitinol may undergo a phase change from Martensite to Austenite, changing its structure. In addition to this phase change ability, Nitinol is also quite flexible.

Similarly, Elgiloy is a metal or super-alloy, also exhibiting flexibility. Elgiloy is slightly more flexible than traditional steel. A skilled artisan will understand that a similarly flexible material or metal may be used in the filter struts.

In addition, a coating may be applied to the device. Such a coating may avoid unintended clotting of blood flow around the device. For example, the sliders and bars may be coated with an anti-coagulation compound to prevent blood clotting within these areas and to keep free movement.

In one embodiment, coating may be accomplished through any means known in the art including chemical vapor deposition, dip coating, spraying, or painting. Preferably, coating provides a uniform layer of the preferred compound. For example, the layer would be 10 microns thick. The chosen coating material may be any means known in the art. In one embodiment, it could be a medical grade polymer to prevent coagulation. For example, the device could be coated with PTX®.

Figure 3:
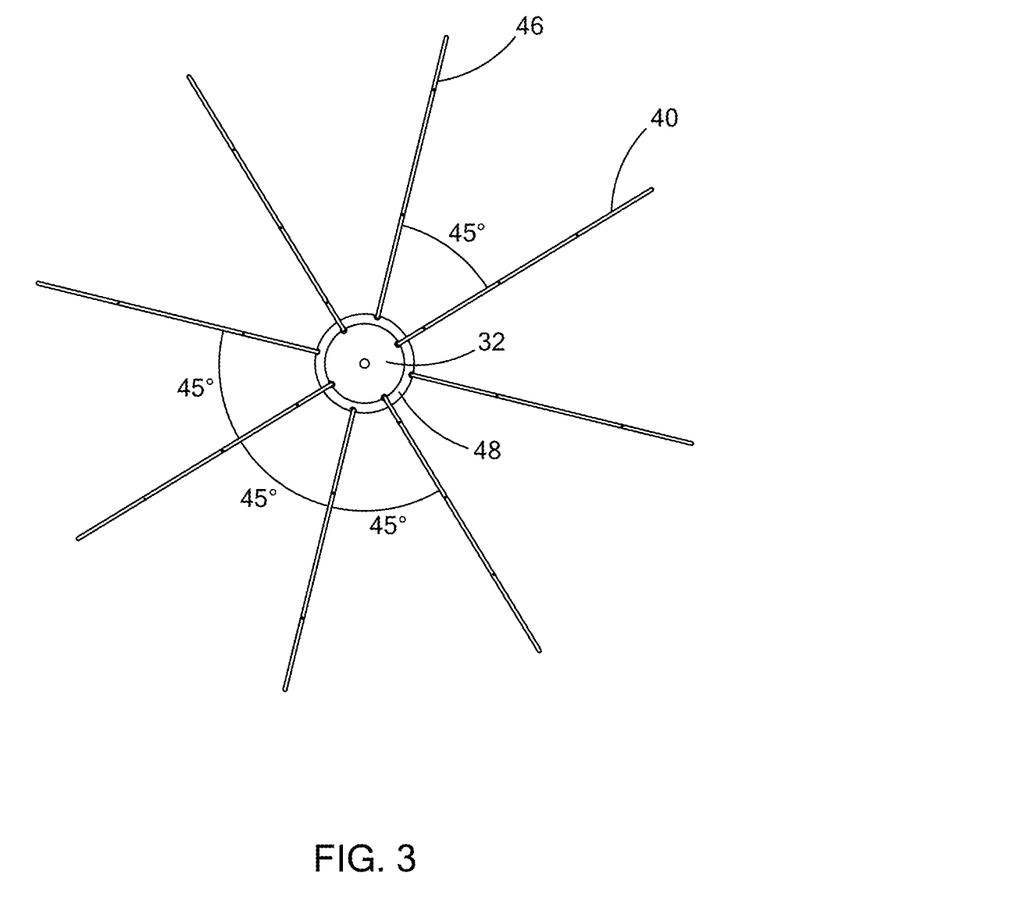
FIG. 3 is an end view of the device in FIG. 1A.

FIG. 3 is a proximal view of the device. In this figure, the first portion 40 may be disposed or positioned about 45 degrees circumferentially around the first end cap 32 from the fourth portion 46. The first portion 40 may be attached to the first end cap 32, and the fourth portion 46 may be attached to the second slider 48. It will be understood that the angles between each filter strut and the adjacent filter strut could be 45 degrees if all struts are equally spaced.

The second portion may be disposed about 45 degrees circumferentially from the third portion as well. In one embodiment, the first portion 40 is a plurality of first portions disposed circumferentially and equally spaced around the first end cap 32. Similarly, the second portion may be a plurality of second portion disposed circumferentially and equally spaced around the second slider.

Figure 4A:
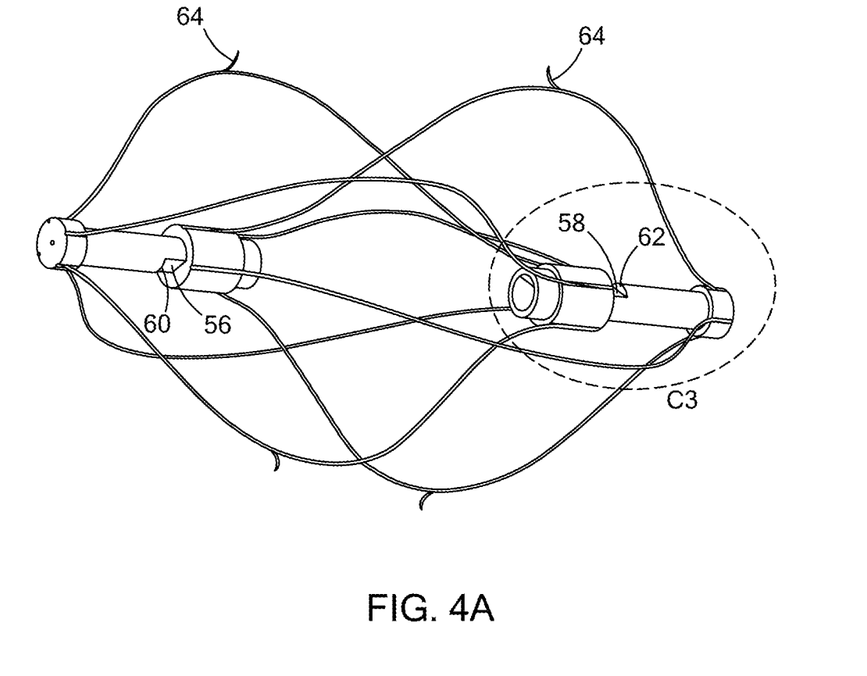
FIG. 4A-4B are side views of one embodiment of the device for filtering in a body vessel in accordance with the present invention.
Figure 4B:
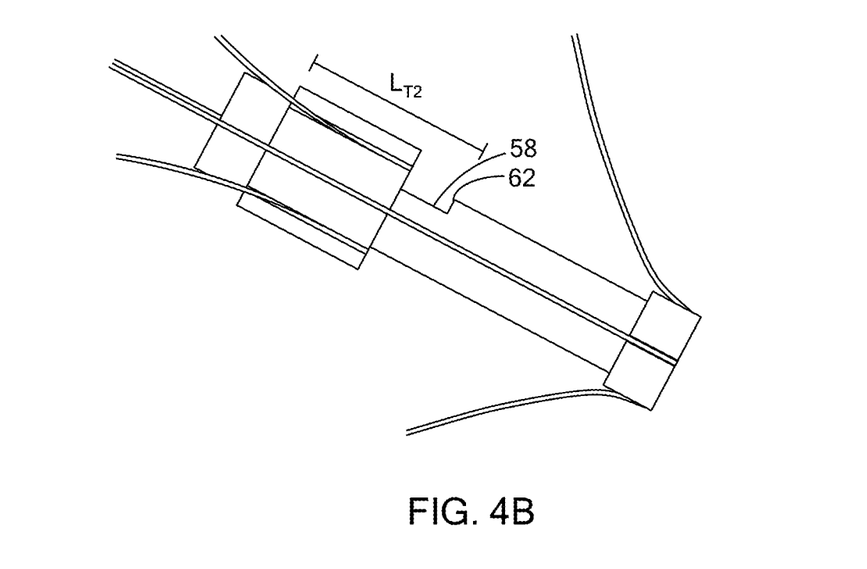

FIGS. 4A-4B depict a second embodiment of the device. In this embodiment, the first and second bars further comprise first and second tracks, respectively. For example, the first bar comprises a first track 56 formed between a proximal track end 60 and the first center cap. The second bar may comprise a second track 58 formed between the second center cap and a distal track end 62. The first slider may be slidably disposed in the first track 56 and the second slider may be slidably disposed in the second track 58.

In this embodiment, the first bore is formed complementary to the first track 56 to maintain the first slider in the first track 56. In addition, the second bore may be formed complementary to the second track 58 to maintain the second slider in the second track 58. FIG. 4B shows a blown-up view of circle C3 in FIG. 4A. Here, the second track 58 is depicted with a second track length $L_{T2}$ extending from the second center cap to the distal track end 62.

In addition, this embodiment shows barbs 64 on the contact portions in FIG. 4A. These barbs may extend into the vessel wall when the device is in filtering position to maintain the device in position and prevent longitudinal movement. Barbs 64 could be utilized on any of the embodiments discussed herein (e.g., FIG. 1A).

Figure 5A:
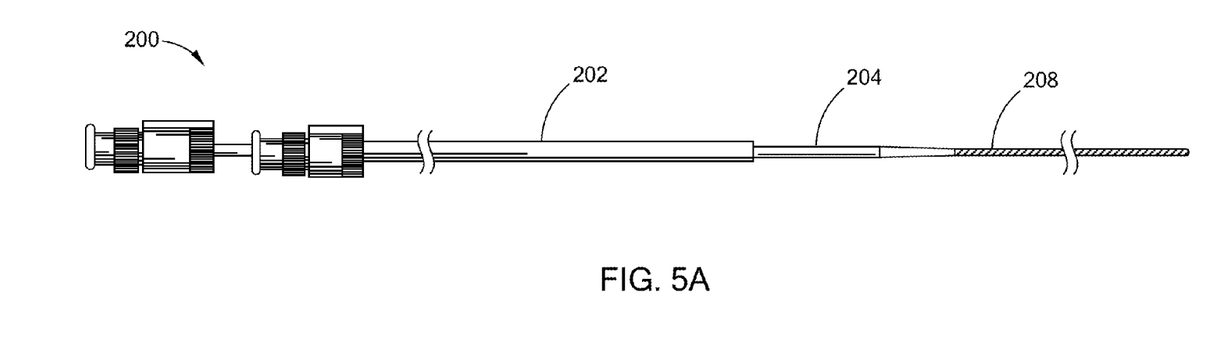
FIG. 5A-5B shows a delivery assembly for introducing the device of FIG. 1A or 4A into the vasculature.
Figure 5B:
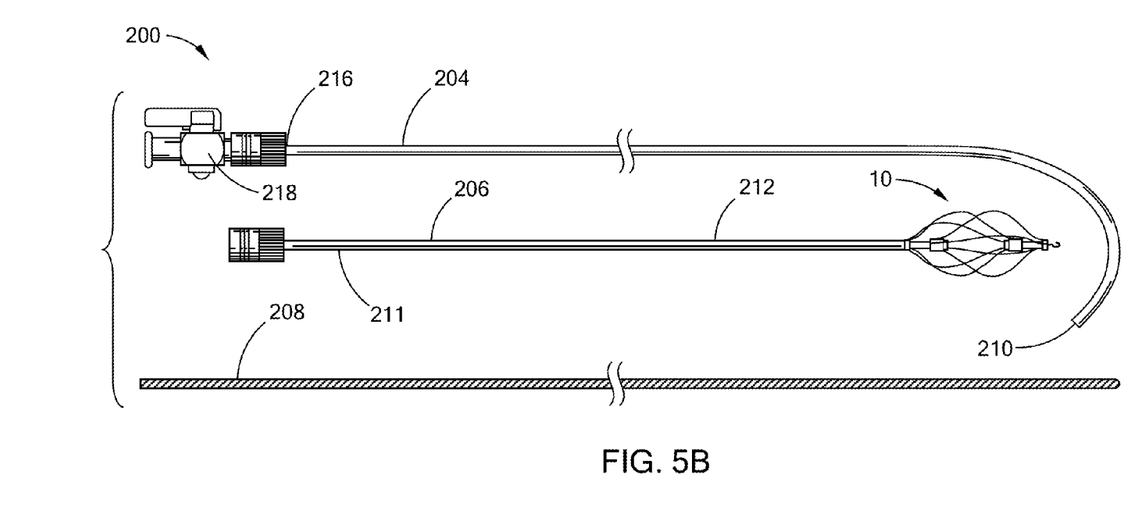

FIGS. 5A-5B depict a delivery or retrieval assembly for the device 10. The device 10 may be delivered or retrieved by way of the Seldinger technique. As shown, the delivery assembly 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention.

The introducer sheath 202 may have any suitable size, for example, between about 3-FR to 8-FR. The introducer sheath 202 serves to allow the outer sheath 204 and an inner member or catheter 206 to be percutaneously inserted to a desired location in the body vessel. The inner member may also include, for example, a stylet. The introducer sheath 202 receives the outer sheath 204 and provides stability to the outer sheath 204 at a desired location of the body vessel. For example, the introducer sheath 202 is held stationary within a common visceral artery, and adds stability to the outer sheath 204, as the outer sheath 204 is advanced through the introducer sheath 202 to a treatment area in the vasculature. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the treatment area. The wire guide 208 provides the outer sheath 204 with a path to follow as it is advanced within the body vessel. The size of the wire guide 208 is based on the inside diameter of the outer sheath 204 and the diameter of the target body vessel.

A needle may also be used. The needle may be used for percutaneously introducing the wire guide into the patient's body through an access site. A cutting device 10 may also be used to expand the access site.

When the distal end 210 of the outer sheath 204 is at the desired location in the body vessel, the wire guide 208 is removed and the device 10, having a proximal segment contacting a distal portion 212 of the inner catheter 206, is inserted into the outer sheath 204. The inner catheter 206 is advanced through the outer sheath 204 for deployment of the device 10 through the distal end 210 to treat the body vessel. The catheter 206 extends from a proximal portion 211 to a distal portion 212 and is configured for axial movement relative to the outer sheath 204.

In this example, the distal portion 212 is shown adjacent to the device. Thus, before deployment, the device 10 is coaxially disposed within the lumen of the outer sheath 204 and removably coupled to the distal portion 212 of the catheter 206, or in the alternative, the device 10 is merely pushed by, but not coupled to, the distal portion 212 of the catheter 206.

The outer sheath 204 further has a proximal end 216 and a hub 218 to receive the inner catheter 206 and device 10 to be advanced therethrough. The size of the outer sheath 204 is based on the size of the body vessel in which it percutaneously inserts, and the size of the device 10.

In this embodiment, the device 10 and inner catheter 206 are coaxially advanced through the outer sheath 204, following removal of the wire guide 208, in order to position the device 10 in the body vessel. The device 10 is guided through the outer sheath 204 by the inner catheter 206, preferably from the hub 218, and exits from the distal end 210 of the outer sheath 204 at a location within the vasculature where occlusion is desired. Thus, the device 10 is deployable through the distal end 210 of the outer sheath 204 by means of axial relative movement of the catheter 206. In order to more easily deploy the device 10 into the body vessel, the device 10 may have a lubricious coating, such as silicone or a hydrophilic polymer, e.g. AQ® Hydrophilic Coating as known in the art.

Likewise, in this embodiment the device 10 may also be retrieved by positioning the distal end 210 of the outer sheath 204 adjacent the deployed device in the vasculature. The inner catheter 206 is advanced through the outer sheath 204 until the distal portion 212 protrudes from the distal end 210 of the outer sheath 204. The distal portion 212 is coupled to a proximal end of the device 10, after which the inner catheter 206 is retracted proximally, drawing the device 10 into the outer sheath 204.

If a hook is present in the device 10, such hook may aid in delivery and retrieval. If a hook is not present, the physician may otherwise grasp a proximal portion of the device 10 for delivery and retrieval.

The device 10 has a collapsed state for delivery and an expanded state for filtering once delivered to the desired location in the body vessel. In the collapsed state, the device 10 is disposed inside the delivery assembly. The device 10 may be self-expanding to the expanded state upon exiting the delivery assembly for filtering (as shown in FIG. 5B). Such self-expansion may be facilitated by using Nitinol.

The assembly described above is merely one example of an assembly that may be used to deploy the device in a body vessel. Of course, other apparatus, assemblies and systems may be used to deploy any embodiment of the device without falling beyond the scope or spirit of the present invention.

Figure 6:
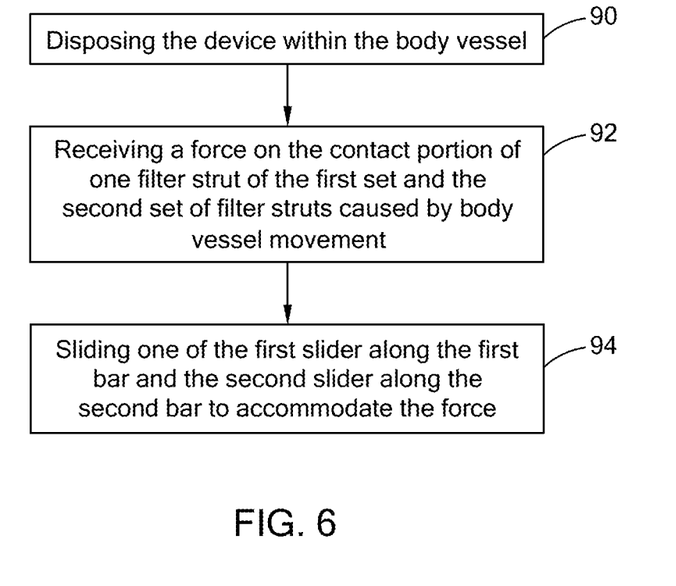
FIG. 6 is a flow diagram of one method of filtering with the medical device of FIG. 1A or 4A from the body vessel in accordance with one example of the present invention.

FIG. 6 depicts a flow diagram of one method of treatment using the device. In step 90, the physician may dispose a device (having any or all of the features discussed herein) within the body vessel. In step 92, the device may receive a force on the contact portion of one filter strut of the first set and the second set of filter struts caused by body vessel movement. In step 94, the device may slide one of the first slider along the first bar and the second slider along the second bar to accommodate the force.

In the embodiment in FIG. 1A, the step of sliding comprises the first slider sliding along the first bar between the first end cap and the first center cap. Additionally in this embodiment, the step of sliding may comprise the second slider sliding along the second bar between the second center cap and the second end cap. In the embodiment of FIG. 4A, the step of sliding may comprise sliding the first slider in the first track between the proximal track end and the first center cap. Additionally in this embodiment, the step of sliding may comprise the second slider sliding in the second track between the second center cap and the distal track end.

Figure 7:
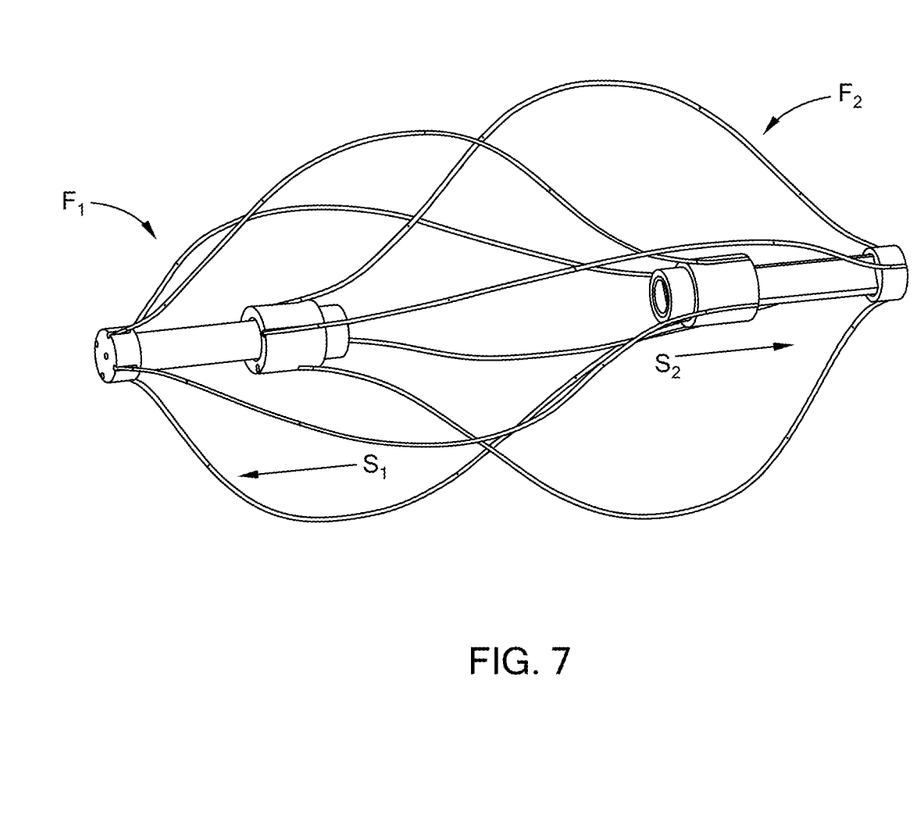
FIG. 7 depicts steps of the method of FIG. 6.

FIG. 7 depicts these method steps of FIG. 6. For example, a first force $F_1$ may push or act on one strut of the first set of filter struts. This first force $F_1$ may slide the second slider in the direction of arrow $S_2$. Alternatively or in addition, a second force $F_2$ may act on one strut of the second set of filter struts (via the contact portion). This second force $F_2$ may slide the first slider in the direction of arrow $S_1$, opposite or independent from $S_2$. This independent motion and accommodation allows the vena cava to remain flexible even with the insertion of the filter device, while still maintaining maximal filtering capacity.

While the present invention has been described in terms of certain preferred embodiments, it will be understood that the invention is not limited to these disclosed embodiments as those having skill in the art may make various modifications without departing from the scope of the following claims.

The invention claimed is:

1. A filter device for filtering a body vessel, the body vessel having a vessel wall, the filter device comprising:

a first bar having a first end comprising a first end cap and extending distally along a first longitudinal length $L_{B1}$ to a second end comprising a first center cap, and a second bar having a third end comprising a second end cap and extending proximally along a second longitudinal length $L_{B2}$ to a fourth end comprising a second center cap, the first end cap being disposed proximal to the second end cap;

a first slider having a first slider body with a first bore formed therethrough defining a first opening and a second opening, the first bar slidably disposed through the first and second openings to allow play between the first bar and first slider, and a second slider having a second slider body with a second bore formed therethrough defining a third opening and a fourth opening, the second bar slidably disposed through the third and fourth openings to allow play between the second bar and second slider; and a first set of filter struts and a second set of filter struts, the first set of filter struts comprising a first filter strut being arcuate and having a first portion attached to the first end cap and extending distally to a second portion, the second portion being attached to the second slider, the second set of filter struts comprising a second filter strut being arcuate and having a third portion attached to the second end cap and extending proximally to a fourth portion, the fourth portion being attached to the first slider, each filter strut having a contact portion to contact the vessel wall wherein the first and second sets of filter struts allow accommodation of body vessel movement.

2. The device of claim 1 wherein the first bar is cylindrical to complement the first bore.

3. The device of claim 2 wherein the second bar is cylindrical to complement the second bore.

4. The device of claim 1 wherein the first slider has a length $L_{S1}$ and the second slider has a length $L_{S2}$, the length $L_{S1}$ being shorter than the first longitudinal length $L_{S1}$ and the length $L_{S2}$ being shorter than the second longitudinal length $L_{B2}$.

5. The device of claim 4 wherein the first bar comprises a first track formed between a proximal track end and the first center cap and the second bar comprises a second track formed between the second center cap and a distal track end wherein the first slider is slidably disposed in the first track and the second slider is slidably disposed in the second track.

6. The device of claim 5 wherein the first bore is formed complementary to the first track to maintain the first slider in the first track.

7. The device of claim 6 wherein the second bore is formed complementary to the second track to maintain the second slider in the second track.

8. The device of claim 1 further comprising a first hook attached to the first end cap and a second hook attached to the second end cap.

9. The device of claim 1 wherein the first portion is disposed about 45 degrees circumferentially from the fourth portion, and the second portion is disposed about 45 degrees circumferentially from the third portion.

10. The device of claim 9 wherein the first end cap has a plurality of first portions disposed circumferentially and equally spaced therearound, and the second slider has a plurality of second portions disposed circumferentially and equally spaced therearound.

11. The device of claim 10 wherein the second end cap has a plurality of third portions disposed circumferentially and equally spaced therearound, the first slider has a plurality of forth portions disposed circumferentially and equally spaced therearound.

12. The device of claim 1 wherein the first set of filter struts comprises four filter struts and the second set of filter struts comprises four filter struts.

13. The device of claim 1 wherein the first end cap has a plurality of first portions disposed circumferentially and equally spaced therearound, the second slider has a plurality of second portions disposed circumferentially and equally spaced therearound, the second end cap has a plurality of third portions disposed circumferentially and equally spaced therearound, the first slider has a plurality of forth portions disposed circumferentially and equally spaced therearound.

14. The device of claim 1 wherein each filter strut comprises a barb adjacent to the contact portion to secure the device to the vessel wall.

15. A method of treatment in a body vessel, the body vessel comprising a vessel wall, the method comprising:
  disposing a device within the body vessel, the device comprising:
  a first bar having a first end comprising a first end cap and extending distally along a first longitudinal length LB1 to a second end comprising a first center cap, and a second bar having a third end comprising a second end cap and extending proximally along a second longitudinal length LB2 to a fourth end comprising a second center cap, the first end cap being disposed proximal to the second end cap;
  a first slider having a first slider body with a first bore formed herethrough defining a first opening and a second opening, the first bar slidably disposed through the first and second openings to allow play between the first bar and first slider, and a second slider having a second slider body with a second bore formed therethrough defining a third opening and a fourth opening, the second bar slidably disposed through the third and fourth openings to allow play between the second bar and second slider;
  and a first set of filter struts and a second set of filter struts, the first set of filter struts comprising a first filter strut being arcuate and having a first portion attached to the first end cap and extending distally to a second portion, the second portion being attached to the second slider, the second set of filter struts comprising a second filter strut being arcuate and having a third portion attached to the second end cap and extending proximally to a fourth portion, the fourth portion being attached to the first slider, each filter strut having a contact portion to contact the vessel wall wherein the first and second sets of filter struts allow accommodation of body vessel movement;
  receiving a force on the contact portion of one filter strut selected from the group of the first set of filter struts and the second set of filter struts;
  sliding one of the first slider along the first bar and the second slider along the second bar to accommodate the force.

16. The method of claim 15 wherein the step of sliding comprises the first slider sliding along the first bar between the first end cap and the first center cap.

17. The method of claim 15 wherein the step of sliding comprises the second slider sliding along the second bar between the second center cap and the second end cap.

18. The method of claim 15 wherein the step of disposing comprises disposing the device wherein the first bar comprises a first track formed between a proximal track end and the first center cap and the second bar comprises a second track formed between the second center cap and a distal track end wherein the first slider is slidably disposed in the first track and the second slider is slidably disposed in the second track.

19. The method of claim 18 wherein the step of sliding comprises the first slider sliding in the first track between the proximal track end and the first center cap.

20. The method of claim 18 wherein the step of sliding comprises the second slider sliding in the second track between the second center cap and the distal track end.

* * * * *